United States Patent [19]

Hausberg et al.

[11] Patent Number: 4,500,541
[45] Date of Patent: Feb. 19, 1985

[54] PHARMACOLOGICALLY ACTIVE CYCLOPROPANE DERIVATIVES

[75] Inventors: Hans-Heinrich Hausberg, Ober-Ramstadt; Jürgen Uhl; Christoph Seyfried, both of Seeheim-Jugenheim; Klaus-Otto Minck, Ober-Ramstadt, all of Fed. Rep. of Germany

[73] Assignee: Merck Patent Gesellschaft Mit Beschränkter Haftung, Darmstadt, Fed. Rep. of Germany

[21] Appl. No.: 505,558

[22] Filed: Jun. 17, 1983

Related U.S. Application Data

[63] Continuation-in-part of Ser. No. 261,820, May 8, 1981, abandoned.

[30] Foreign Application Priority Data

May 9, 1980 [DE] Fed. Rep. of Germany ....... 3017812

[51] Int. Cl.³ .................. A61K 31/36; A61K 31/135; A01N 9/20; C07C 93/06
[52] U.S. Cl. ................. 514/466; 260/465 E; 549/437; 564/443; 564/346; 514/655
[58] Field of Search ....................... 564/443; 549/437; 424/282, 330

[56] References Cited

U.S. PATENT DOCUMENTS 3,253,040  5/1966  Potter et al. ........................ 564/346
3,928,426  12/1975 Welstead, Jr. ...................... 424/311
4,207,343  6/1980  Lavagnino et al. ................. 424/316

FOREIGN PATENT DOCUMENTS 0196386 3/1958 Austria.

Primary Examiner—Ethel G. Love
Attorney, Agent, or Firm—Millen & White

[57] ABSTRACT

Cyclopropane derivatives of the formula

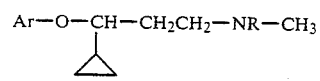

wherein Ar is phenyl or phenyl monosubstituted or polysubstituted by F, Cl, Br, $C_{1-4}$ alkyl, $C_{1-4}$ alkoxy, $C_{2-4}$ alkenyloxy, $C_{1-4}$ alkylthio, OH, SH, CN, methylenedioxy or $CF_3$; and R is H, $C_{1-4}$ alkyl or benzyl, or a physiologically acceptable acid addition salt thereof, have valuable pharmacological properties, e.g., as antidepressants.

11 Claims, No Drawings

PHARMACOLOGICALLY ACTIVE CYCLOPROPANE DERIVATIVES

This application is a continuation-in-part of application Ser. No. 261,820, filed 5/8/81 now abandoned.

The present invention relates to new pharmacologically active cyclopropane derivatives.

SUMMARY OF THE INVENTION

It is an object of one aspect of this invention to provide new compounds which can be used for the preparation of medicaments.

Upon further study of the specification and appended claims, further objects and advantages of this invention will become apparent to those skilled in the art.

These objects have been achieved by providing compounds of formula I

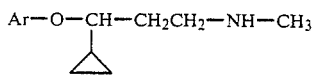    I in which Ar is phenyl or phenyl monosubstituted or polysubstituted by F, Cl, Br, alkyl, alkoxy, alkenyloxy and/or alkylthio, in each case, of not more than 4 C atoms, OH, SH, CN, methylenedioxy and/or $CF_3$ and R is H, alkyl of 1–4 C atoms or benzyl, and the physiologically acceptable acid addition salts thereof.

DETAILED DISCUSSION

In the radicals Ar and R, alkyl is preferably methyl, or also ethyl, n-propyl, isopropyl, n-butyl, isobutyl, sec-butyl or tert-butyl. Alkoxy (in the radical Ar) is preferably methoxy, or also ethoxy, n-propoxy, isopropoxy, n-butoxy, isobutoxy, sec-butoxy or tert-butoxy. Alkenyloxy (in the radical Ar) is preferably allyloxy, or also vinyloxy, propenyloxy, isopropenyloxy, 1-buten-1- or -2-yloxy, 2-buten-1- or -2-yloxy, 3-buten-1- or -2-yloxy, 2-methyl-1-propen-1- or -2-yloxy or 2-methyl-2-propen-1-yloxy.

Alkylthio (in the radical Ar) is preferably methylthio, or also ethylthio, n-propylthio, isopropylthio, n-butylthio, isobutylthio, sec-butylthio or tert-butylthio.

The radical Ar is preferably a monosubstituted phenyl group, but can also be, in particular, an unsubstituted phenyl group or a disubstituted phenyl group, or also a trisubstituted, tetrasubstituted or pentasubstituted phenyl group.

Specifically, the radical Ar is preferably fluorophenyl, chlorophenyl, methoxyphenyl, allyloxyphenyl, methylthiophenyl, hydroxyphenyl, mercaptophenyl, cyanophenyl or, in particular, trifluoromethylphenyl and specifically, in particular, m- or p-fluorophenyl, p-chlorophenyl, o-, m- or p-methoxyphenyl, o-allyloxyphenyl, p-methylthiophenyl or p-trifluoromethylphenyl. Furthermore, Ar is preferably o-, m- or p-tolyl, o-, m- or p-ethylphenyl, o-fluorophenyl, o- or m-chlorophenyl, o-, m- or p-bromophenyl, o-, m- or p-ethoxyphenyl, o-, m- or p-n-propoxyphenyl, O-, m- or p-isopropoxyphenyl, o-, m- or p-vinyloxyphenyl, m- or p-allyloxyphenyl, o- or m-methylthiophenyl, o-, m- or p-ethylthiophenyl, o-, m- or p-hydroxyphenyl, o-, m- or p-mercaptophenyl, o-, m- or p-cyanophenyl, 3,4-methylenedioxyphenyl or o- or m-trifluoromethylphenyl. Among the disubstituted phenyl groups, dimethoxyphenyl, in particular 3,4-dimethoxyphenyl, is preferred and among the trisubstituted phenyl groups, trimethoxyphenyl, in particular 3,4,5-trimethoxyphenyl, is preferred.

The radical R is preferably H and is also preferably methyl or benzyl, and furthermore, in particular, ethyl.

Accordingly, the present invention relates in particular to those compounds of this invention in which at least one of the radicals has one of the meanings indicated above and in particular one of the meanings indicated above as being preferred. Several preferred groups of compounds and the corresponding salts can be expressed by the following partial formulae Ia to Ie, which correspond to the formula I and in which the radicals are not designated in more detail have the meaning indicated for formula I, but in which in Ia
Ar is phenyl or phenyl monosubstituted by F, Cl, $CH_3O$, $CH_2=CHCH_2O$, $CH_3S$, OH, SH, CN OR $CF_3$ and
R is H, $CH_3$ or benzyl;

in Ib
Ar is m- or p-fluorophenyl, p-chlorophenyl, o-, m- or p-methoxyphenyl, o-allyloxyphenyl, p-methylthiophenyl or p-trifluoromethylphenyl and
R is H, $CH_3$ or benzyl;

in IC
Ar is m- or p-fluorophenyl, p-chlorophenyl, o-, m- or p-methoxyphenyl, o-allyloxyphenyl, p-methylthiophenyl or p-trifluoromethylphenyl and
R is H or $CH_3$;

in Id
Ar is o-methoxyphenyl or p-trifluoromethylphenyl and
R is H, $CH_3$ or benzyl; and in Ie
Ar is p-trifluoromethylphenyl and
R is H, $CH_3$ or benzyl.

The compounds of this invention can possess one or more asymmetric carbon atoms. They can therefore be in the form of racemates, or, if several asymmetric carbon atoms are present, in the form of mixtures of several racemates and also in diverse optically active forms.

The present invention also relates to a process for the preparation of compounds of formula I and of their physiologically acceptable acid addition salts, comprising reacting a phenol of formula II Ar—OH  II in which Ar is as defined above, or one of its salts, with an amine of formula III

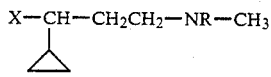    III in which X is Cl, Br, I or OH and R is as defined above, or with one of its reactive derivatives; or reacting a cyclopropane derivative of formula IV

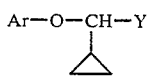    IV in which Y is $-CH_2CH_2X$ or $-CH=CH_2$ and Ar and X are as defined above, or one of its reactive derivatives, with an amine of formula V

HNR—CH₃    V in which R is as defined above; or treating an amine of formula VI

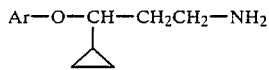
Ar—O—CH—CH₂CH₂—NH₂    VI in which Ar is as defined above, with an alkylating agent; or treating with a solvolyzing agent, a compound which corresponds to formula I but additionally contains a solvolytically detachable group in place of a hydrogen atom; or treating with a reducing agent, a compound which corresponds to formula I but contains one or more reducible groups and/or one or more C—C and/or C—N multiple bonds in place of hydrogen atoms; and/or optionally, converting in a compound of formula I, a secondary amino group by treatment with an alkylating or benzylating agent into the corresponding tertiary amino group, and/or converting a hydroxyl group by treatment with an alkylating or alkenylating agent into the corresponding alkoxy or alkenyloxy group, and/or converting a mercapto group by treatment with an alkylating agent into the corresponding alkylthio group, and/or converting an N-benzyl group by treatment with a debenzylating agent (stepwise if desired) into an NH group, and/or splitting an alkoxy group and/or alkylthio group with the formation of a hydroxyl group and/or mercapto group, and/or converting a resulting base of formula I by treatment with an acid into one of its physiologically acceptable acid addition salts.

In other respects, the compounds of formula I are prepared by methods known per se, such as are described in the literature (for example in the standard works such as Houben-Weyl, Methoden der Organischen Chemie (Methods of Organic Chemistry), Georg-Thieme-Verlag, Stuttgart; and Organic Reactions, John Wiley and Sons, Inc., New York), and specifically are prepared under reaction conditions which are known and suitable for these reactions. It is also possible to make use of variants which are known per se and are not mentioned in more detail herein.

If desired, the starting materials of formulae II and III can also be formed in situ, in such a way that they are not isolated from the reaction mixture but are immediately further reacted to give the compounds of formula I.

The compounds of the formula I are preferably obtained by reacting the phenols of formula II, or preferably, their salts, with the amines of formula III.

The phenols of formula II are known in most cases and can be prepared by methods which are in themselves known, for example, by splitting corresponding benzyl or methyl ethers.

In the compounds of formulae III and IV, X is preferably Cl or Br. Reactive derivatives of these compounds include, in particular, the reactive esters of the alcohols of formulae II and IV(X=OH), preferably the corresponding alkylsulfonates (in which the alkyl group possesses 1-6 C atoms) and the corresponding arylsulphonates (in which the aryl group possesses 6-10 C atoms), for example the corresponding methane-, benzene-, p-toluene- or naphthalene-1- or -2-sulphonates.

The bases of formula III can be prepared by methods which are in themselves known. Thus, for example, the alcohols of formula III (X=OH) are obtainable by a Mannich reaction, from cyclopropyl methyl ketone, formaldehyde and amines of the formula HNR-CH₃ to produce ketones of the formula cyclopropyl-COCH₂C-H₂—NR—CH₃ and subsequent reduction of these ketones; the compounds of formula III (X=Cl, Br or I) are obtainable from the alcohols and inorganic halides, e.g., as SOCl₂, PBr₃ or HI; and the sulphonates are obtainable by esterification of the alcohols with the corresponding sulphonyl chlorides. Among the amines of formula III, the tertiary amines (in which R is not H) are also accessible from the secondary amines (III, R=H) by alkylation or benzylation. Conversely, the secondary amines (III, R=H) can be obtained from the corresponding N-alkyl or N-benzyl derivatives (III, R=alkyl of 1-4 C atoms or benzyl) by dealkylation or debenzylation with ethyl chloroformate, or trichloroethyl chloroformate.

Prior to the reaction with the amine III, the phenol II is preferably first converted to a salt, in particular to a metal salt, for example an alkali metal salt (Li salt, Na salt or K salt) or thallium salt. II can be reacted with a reagent which forms a metal salt, for example with an alkali metal (for example Na), an alkali metal hydride or alkali metal amide (for example LiH, NaH, NaNH₂ or KNH₂), a metal alcoholate (in which the alcohol portion preferably possesses 1-4 C atoms, for example lithium methylate, ethylate or tert-butylate, sodium methylate, ethylate or tert-butylate, potassium methylate, ethylate or tert-butylate, or thallium methylate, ethylate or tert-butylate), an organo-metallic compound (for example butyl-lithium, phenyl-lithium or phenyl-sodium), or a metal hydroxide, metal carbonate or metal bicarbonate (for example of Li, Na, K or Ca). The preparation of the salt is advantageously carried out in the presence of a solvent or solvent mixture. Suitable solvents include, for example, hydrocarbons (e.g., hexane, benzene, toluene or xylene), ethers (e.g., diethyl ether, diisopropyl ether, tetrahydrofuran (THF), dioxane or diethylene glycol dimethyl ether), amides, such as dimethylformamide (DMF), and alcohols, (e.g., methanol or ethanol).

The phenol II, or its salts, is preferably reacted with the amine III in the presence of a diluent, for example of that solvent which has been used for the preparation of the salt; but this solvent can be replaced by or diluted with another solvent.

The reaction is generally carried out at temperatures of approximately −20° to 150°, preferably 20° to 120°.

The phenolate can also be formed in situ. In this case, the phenol II and the amine III are allowed to react with one another in the presence of a base.

A variant of the reaction consists in reacting the phenol of formula II with a hydroxyamine of formula III (X=OH) in the presence of a dehydrating agent, for example of an azodicarboxylic acid dialkyl ester, in the presence of triphenylphosphine, in an inert solvent, such as THF, at approximately −10° to +30°.

The cyclopropane derivatives of formula I are also obtainable by reacting compounds of formula IV with amines of formula V.

The starting materials of formula IV (Y=—CH₂-H₂OH) are obtainable, for example, by reacting cyclopropyl cyanide with organometallic compounds of the formula M—CH₂CH(O-alkyl)₂ (in which M is Li, MgCl or MgBr) and then hydrolyzing the reaction product to 3,3-dialkoxy-1-cyclopropyl-propan-1-ones, reducing the latter to 3,3-dialkoxy-1-cyclopropyl-propan-1-ols, etherifying these with phenols of the formula Ar-OH to give the corresponding 3,3-dialkoxy-1-cyclopropyl-1-aryloxy-propanes, hydrolyzing the latter to 3-cyclopropyl-3-aryloxypropanals and reducing these. From the compounds of formula IV (Y=—CH$_2$CH$_2$OH), compounds of formula IV (Y=—CH=CH$_2$) are obtainable by dehydration, and compounds of formula IV (Y=—CH$_2$CH$_2$Cl, —CH$_2$CH$_2$Br or —CH$_2$CH$_2$I) are obtainable by reaction with inorganic halides, e.g., SOCl$_2$, PBR$_3$ or HI, and the corresponding sulphonates are obtainable by esterifying the alcohols (IV, Y=CH$_2$CH$_2$OH) with sulphonyl chlorides.

The reaction of the compounds of formulae IV and V is effected under alkylating conditions, preferably in the presence of one of the inert solvents mentioned, at temperatures of approximately 20° to 140°, preferably 80° to 120°. If readily volatile starting materials of formula V are used, it can be advantageous to carry out the reaction under pressure (up to about 100 atmospheres).

The cyclopropane derivatives of formula I can also be prepared from amines of formula VI by alkylation, in particular methylation.

The amines of formula IV can be prepared, for example, from the compounds of formula IV and ammonia.

Alkylation of the amines of formula VI is preferably effected under the same conditions as the reaction of IV and V.

The amines of formula VI can be subjected to a condensation reaction with aldehydes or ketones, with the formation of aldehyde-ammonia compounds, Schiff bases or enamines. These can then be either hydrogenated or treated with an alkylating agent and the resulting quaternary salt can then be hydrolyzed. For example, an amine of formula VI can be converted, by a condensation reaction with benzaldehyde, to the N-benzylidene compound and this can be converted, by means of a methyl halide, into one of its quaternary salts, which can then be converted, for example by treatment with aqueous alcohol, with the elimination of benzaldehyde, into a secondary amine of formula I (R=H). It is also possible to carry out alkylation with aldehydes or ketones under reducing conditions, in which case the corresponding aldehyde-ammonias are formed as intermediate products. For example, it is possible to introduce one or two methyl groups using formaldehyde in the presence of formic acid. Furthermore, alkylation can be effected with an alcohol in the presence of Raney nickel.

Furthermore, in a compound which corresponds to formula I but which additionally contains a solvolytically detachable group (preferably an N-acyl, O-acyl, S-acyl, N-cyano group) in place of a hydrogen atoms, this group can be split off by treatment with a solvolyzing agent.

Preferred starting materials for this solvolysis are those of formula VII

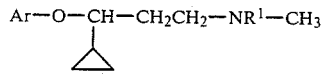

Ar—O—CH—CH$_2$CH$_2$—NR$^1$—CH$_3$    VII in which R$^1$ is CN or an acyl group having 1-7 C atoms, preferably acetyl, trifluoroacetyl or benzoyl, and Ar is as defined above.

The starting materials of formula VII are obtainable for example, by reacting compounds of the formula IV with compounds of the formula HNR$^1$—CH$_3$, or by reacting compounds of the formula cyclopropyl—CHX—CH$_2$—CH$_2$—NR$^1$—CH$_3$ with phenols of the formula Ar—OH(II).

Starting materials which correspond to formula I but carry, in the radical Ar, an acyloxy or acylthio group, having, in each case, 1-7 C atoms in the acyl radical, in place of an OH or SH group are also suitable.

Solvolysis of these compounds is preferably effected by the action of a solvent, e.g., water (hydrolysis) or of an alcohol having, preferably, 1-4 C atoms (alcoholysis), in the presence of an acid or basic catalyst, for example of a mineral acid, e.g., sulphuric acid or hydrochloric acid, of a metal hydroxide, e.g., sodium hydroxide, potassium hydroxide, calcium hydroxide, barium hydroxide, lead hydroxide or silver hydroxide, or of a metal salt or ammonium salt, e.g., sodium carbonate or potassium carbonate or ammonium chloride. The alcohols used are preferably methanol, ethanol or isopropanol, and it is also possible to use mixtures of water with one of these alcohols. Solvolysis is preferably effected at temperatures of approximately 0° to approximately 120°.

Specifically, hydrolysis is preferably effected by boiling for 1-24 hours with aqueous, aqueous-alcoholic, aqueous-ethyleneglycollic or alcoholic sodium-hydroxide solution or potassium hydroxide solution.

The cyclopropane derivatives of formula I can also be prepared by reduction of corresponding starting materials which additionally contain reducible groups and/or C—C and/or C—N double bonds or triple bonds.

Among the reducible starting materials, preferred are those of the formula VIII

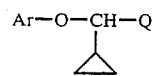

Ar—O—CH—Q    VIII in which Q is —CH=CH—NR—CH$_3$, —CH$_2$CH=N—R, —CH$_2$—CH$_2$—N=CH$_2$, —CO—CH$_2$—N-R—CH$_3$, —CH$_2$—CO—NR—CH$_3$ or —CH$_2$—CH$_2$—NR$^2$—CH$_3$ and R$^2$ is an amino-protective group which is detachable by hydrogenolysis or is a hydroxyalkyl, oxoalkyl, alkenyl or alkynyl group, having in each case, not more than 4 C atoms, and Ar and R are as defined above.

The compounds of formula VIII can be obtained, for example, by reacting phenols of the formula Ar-OH(II) with cyclopropane derivatives of the formula cyclopropyl—CHX—Q (in which Ar, X and Q are as defined above). Schiff bases of formula VIII, in which Q is —CH$_2$—CH=N—R, can also be obtained from the above mentioned 3-cyclopropyl-3-aryloxypropanals and ammonia or amines of the formula R—NH$_2$; and amides of formula VIII, in which Q is —CH$_2$—CO—N-R—CH$_3$, can also be obtained by amidation of corresponding 3-cyclopropyl-3-aryloxypropanoic acids or their esters.

Further suitable starting materials include, for example, those which correspond to formula I but carry, in the radical Ar, a benzyloxy or benzylthio group in place of an OH or SH group.

The starting materials of formula VIII and the other reducible starting materials can, for example, by converted to the compounds of formula I by catalytic hydrogenation, with nascent hydrogen, with complex metal hydrides or with other chemical reducing agents.

The reduction methods which are suitable for the individual starting materials in general depend on the nature of the specific group involved and are well known to those skilled in the art from the data given in the literature. Thus, for example, Schiff bases and olefinic compounds can particularly advantageously be catalytically hydrogenated. Reduction of the acid amides, on the other hand, is particularly advantageously effected with complex metal hydrides or with diborane.

Suitable catalysts for catalytic hydrogenation reactions include, for example, noble metal catalysts, nickel catalysts or cobalt catalysts, and also mixed catalysts, e.g., copper/chromium oxide. Noble metals which can be used are, in particular, platinum and palladium, which can be on supports (for example on charcoal, calcium carbonate or strontium carbonate), in the form of oxides (for example platinum oxide) or in a finely divided form. Nickel and cobalt catalysts are preferably employed in the form of the Raney metals. The hydrogenation can preferably be carried out under pressures of approximately 1 to 200 atmospheres and at temperatures of approximately $-80°$ to $+150°$. The hydrogenation is effected in the presence of an inert solvent, for example of an alcohol, e.g., methanol, ethanol or isopropanol, of a carboxylic acid, e.g., acetic acid, of an ester, e.g., ethyl acetate, or of an ether, e.g., tetrahydrofuran (THF) or dioxane. It is also possible to use solvent mixtures, for example also water-containing mixtures. Hydrogenation under mild conditions, for example at temperatures of 0° to 30° under normal pressure, is preferred.

Furthermore, complex metal hydrides, e.g., $LiAlH_4$, $NaBH_4$ or $NaAl(OCH_2CH_2OCH_3)_2H_2$ and also diborane can be employed as reducing agents, if desired with the addition of catalysts, e.g., $BF_3$, $AlCl_3$, or LiBr. Suitable solvents for this reaction are, in particular, ethers, e.g., diethyl ether, THF, dioxane, 1,2-dimethoxyethane or diglyme, and also hydrocarbons, e.g., benzene. For a reduction with $NaBH_4$, suitable solvents are, in particular, alcohols, e.g., methanol or ethanol. With this method, the reduction is preferably carried out at temperatures of approximately $-80°$ to $+150°$ and in particular of approximately 20° to 120°.

Another suitable reduction method is reaction with nascent hydrogen. The latter can be generated, for example, by treating metals with acids or bases. Thus, for example, the system zinc/acid, zinc/alkali metal hydroxide solution, iron/acid or tin/acid can be used. Suitable acids include, for example, hydrochloric acid or acetic acid. An alkali metal, e.g., sodium, in an alcohol, e.g., ethanol, isopropanol, n-butanol, amyl alcohol or isoamyl alcohol, or in phenol, can also be used as the reducing agent, as can also, for example, an aluminum/nickel alloy in alkaline-aqueous or alkaline-aqueous-alcoholic solution, and also sodium amalgam or aluminum amalgam in aqueous-alcoholic or aqueous solution. With these methods, the reaction temperatures are approximately 0° to approximately 150°, preferably approximately 20° to 120°.

Furthermore, if desired, secondary amines of the formula I (R=H) can be alkylated on the nitrogen atom, in which case tertiary amines of formula I (R-alkyl of 1-4 C atoms) are obtained. Suitable N-alkylating agents include, for example, the corresponding alkyl halides, for example methyl chloride, methyl bromide, methyl iodide, ethyl chloride, ethyl bromide, ethyl iodide, n-propyl chloride, n-propyl bromide or n-propyl iodide and the like, and also the corresponding dialkyl sulphates, such as dimethyl sulphate, and the corresponding sulphonic acid alkyl esters, such as methyl p-toluenesulphonate. A methyl group can also be introduced, for example, by treatment with formic acid and aqueous formaldehyde solution, preferably by heating for several hours at temperatures of 50° to 100°. In general, the N-alkylation is preferably carried out in the presence or absence of an inert solvent at temperatures of approximately 0° to approximately 120°, preferably 40° to 100°, and it is also possible for the reaction mixture to contain a catalyst, preferably a base, e.g., potassium tert-butylate.

Alkylation also proceeds by treatment of a secondary amine I (R=H) with an aldehyde or ketone in the presence of hydrogen and a hydrogenation catalyst (for example Raney nickel) at temperatures of approximately 50° to 100° and under pressures of approximately 1 to 200 atmospheres; thus, with acetone, the corresponding isopropyl compound I (R=isopropyl) is obtained.

Alkylation is also possible in several stages. For example, an amine of formula I (R=H) can first be acylated in a manner is in itself known (for example acetylated by treatment with acetic anhydride/pyridine) and the resulting N-acylation product (for example N-acetylation product) can then be reduced to the desired tertiary amine, for example using a complex metal hydride such as $LiAlH_4$ in an inert solvent, such as diethyl ether or THF, preferably at temperatures of 20° to 60°.

In an entirely analogous manner, a secondary amine of formula I (R=H) can be treated with benzylating agents (for example benzyl halides, e.g., benzyl chloride or benzyl bromide), in which case tertiary amines of formula I (R=benzyl) are formed.

In a similiar manner, a phenol of formula I (Ar=phenyl substituted by one or more OH groups) can be alkylated or alkenylated, a compound of formula I (Ar=phenyl substituted by one or more alkoxy and/or alkenyloxy groups) being obtained. Suitable alkylating agents include, for example, the above-mentioned alkyl halides, dialkyl suphates and sulphonic acid alkyl esters, and suitable alkenylating agents include the corresponding alkenyl halides (for example allyl chloride, allyl bromide or allyl iodide).

The O-alkylation (or alkenylation) is preferably carried out at temperatures of approximately 0° to approximately 150°, preferentially 20° to 100°, in an inert solvent, for example an alcohol, e.g., methanol or ethanol, a hydrocarbon, e.g., benzene, an amide, e.g., DMF, an ether, e.g., THF, or an amine, e.g., pyridine. If halides are used, the reaction is preferably carried out in the presence of a base, e.g., NaOH, KOH, triethylamine or pyridine, and an excess of this base can serve as the solvent.

S-Alkylation of mercaptans of formula I (Ar=a phenyl group substituted by one or more SH groups) is possible in an entirely analogous manner, the corresponding alkylthio compounds being obtained.

Furthermore, in a compound of formula I (R=benzyl), the benzyl group can be removed by methods which are in themselves known, for example by hydrogenolysis in the presence of a noble metal catalyst or stepwise with the aid of a dealkylating agent, for example by reaction with ethyl chloroformate, phenyl chloroformate, trichloromethyl chloroformate or 2,2,2-trichloroethyl chloroformate in the presence of a base, to give the corresponding urethane, which is then split by reduction, for example using zinc/acetic acid, or by hydrolysis, for example with a base.

Ethers of formula I (Ar=phenyl substituted by one or more alkoxy groups) can be split by methods which are known from the literature. The corresponding phenols of formula I (Ar=phenyl substituted by one or more OH groups) are formed. For example, the ethers can be split by treatment with HBr or HI in aqueous or acetic acid solution, by heating with Lewis acids, e.g., AlCl$_3$ or boron trihalides, or by melting with pyridine hydrohalides or aniline hydrohalides, preferably pyridine hydrochloride, at about 150°-250°.

Analogously, thioethers of formula I (Ar=phenyl substituted by one or more alkythio groups) can be split to give the corresponding mercapto compounds of formula I (Ar=phenyl substituted by one or more mercapto groups).

A resulting base of formula I can be converted with an acid to the corresponding acid addition salt. Acids suitable for this reaction are those which give physiologically acceptable salts. Thus, it is possible to use inorganic acids, for example sulphuric acid, hydrogen halide acids, e.g., hydrochloric acid or hydrobromic acid, phosphoric acids, e.g., orthophosphoric acid, nitric acid or sulphamic acid, or also organic acids, specifically aliphatic, alicyclic, araliphatic, aromatic or heterocyclic monobasic or polybasic carboxylic, sulphonic or sulphuric acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenyl-propionic acid, citric acid, gluconic acid, ascorbic acid, nicotinic acid, isonicotoinic acid, methaneor ethane-sulphonic acid, ethanedisulphonic acid, 2-hydroxyethanesulphonic acid, benzenesulphonic acid, p-toluenesulphonic acid, naphthalene-mono- and -di-sulphonic acids or laurylsulphuric acid. The free bases of formula I can, if desired, be liberated from their salts by treatment with strong bases, such as sodium hydroxide or potassium hydroxide, sodium carbonate or potassium carbonate.

It has been found that the compounds of formula I and their physiologically acceptable acid addition salts possess valuable pharmacological properties. In particular, they display effects on the central nervous system, above all antidepressant effects. Specifically, a reserpine-antagonistic effect (detectable, for example, against reserpine in mice, by a method based on that of Askew, Life Science, Volume 10 (1963) pages 725-730), an anticataleptic effect (detectable, for example, against tetrabenazine in rats, by a method based on that of Giurgea et al., Medicina Experimentalis, Volume 9, (1963), pages 249-262) and an antiptotic effect (detectable, for example, against reserpine by a method based on that of Domenjoz and Theobald, Arch. int. pharmacodyn., Volume 120 (1959) pages 450 et seq., with evaluation by the method of Rubin et al. J. Pharmacol. Exp. Therap., Volume 120, (1957), pages 125-136) can be demonstrated. Furthermore, the effect of 5-hydroxytryptophane in mice (method: similar to that of Ross et al., Acta pharmacol. et toxicol., Volume 39 (1976), pages 152-166) can be potentiated. The effects, on the central nervous system, of stimulation and a rise in temperature, which can be initiated by D-amphetamine sulfate (for example 1.5 mg/kg administered subcutaneously 1 hour after the test substance, which is also administered subcutaneously) and aggregation (placing 5 rats together in one glass case) (method of Müller-Calgan et al., in Zippel, H. P. (editor): Memory and Transfer of Information, Plenum Press, New York—London, 1973, pages 87-125) can be intensified and/or prolonged. The substances also have an influence on the biogenic amines of the central nervous system. Thus, for example, in vitro they result in inhibition of the absorption of noradrenalin, 5-hydroxy-tryptamine and dopamine (method: Kannengiesser et al., Biochem. Pharmacol. Volume 22 (1973), pages 73-84); in synaptosomes and in vivo (method: Carlsson et al., Europ. J. Pharmacol., Volume 5 (1969), pages 357-366; 367-373) they inhibit the liberation of catecholamine and serotonine which is induced in the brain by tyramine derivatives. Furthermore, the compounds antagonise the lowering of the serotonine level which is caused by p-chloroamphetamine in rats on oral administration (method: Fuller et al., Biochem. Pharmacol., Volume 27 (1978), pages 193-198). Furthermore, hypotensive and spasmolytic effects arise and these can be detected by the methods customarily used for this purpose.

Compounds of formula I and their physiologically acceptable acid addition salts can therefore be used as medicinally active compounds and also as intermediate products for the preparation of other medicinally active compounds.

The present invention thus also relates to the use of the compounds of formula I and their physiologically acceptable salts for the preparation of pharmaceutical formulations, especially by non-chemical means. For this purpose, the compounds can be brought, together with at least one excipient or auxiliary and, optionally, in combination with one or more other active compounds, into a suitable dosage form.

The invention also relates to agents, in particular pharmaceutical formulations, containing a compound of formula I and/or one of its physiologically acceptable acid addition salts. These formulations can be employed as medicaments in human medicine or veterinary medicine. Excipients which can be used are organic or inorganic substances which are suitable for enteral (for example oral) or parenteral administration or topical application and do not react with the new compounds, for example, water, vegetable oils, benzyl alcohols, polyethylene glycols, gelatin, carbohydrates, e.g., lactose or starch, magnesium stearate, talc or white petroleum jelly. The formulations used for enteral administration are, in particular, tablets, dragees, capsules, syrups, juices, drops or suppositories; for parenteral administration are solutions, preferably oily or aqueous solutions, or also suspensions, emulsions or implants; and for topical application are ointments, creams or powders. The new compounds can also be lyophilized and the resulting lyophilizates are used, for example, to prepare injection preparations. The indicated formulations can be sterilized and/or contain auxiliaries, such as lubricants, preservatives, stabilizers and/or wetting agents, emulsifiers, salts for influencing the osmotic pressure, buffer substances, dyestuffs, flavorings and/or aroma generating substances. They can also, if desired, contain one or more further active compounds, for example one or more vitamins.

The invention also relates to the use of the compounds of formula I and their physiologically acceptable acid addition salts in combating ailments, in particular depressions of diverse etiology and symptomatology, and also to their use in the therapeutic treatment of the human or animal body.

As a rule, the substances according to this invention are administered analogously to known, commercially available psychopharmaceutical agents (for example imipramine), preferably in dosages of approximately 2 to 500 mg, and in particular 10 to 50 mg per dosage unit. The daily dose is preferably approximately 0.05 to 10 mg/kg of body weight. The particular dose for each specific patient depends, however, on very diverse factors, for example on the effectiveness of the particular compound employed, on the age, body weight, general state of health, sex, and diet of the patient, on the time and mode of administration, on the rate of elimination, on the combination of medicaments employed and on the severity of the particular aliment to which the therapy applies. Oral administration is preferred.

For example, in determining suitable dosages and regimens conventional considerations will apply, including a compassion of differential potencies of a compound of this invention and of a known compound, e.g., imipramine, using standard protocols, e.g., one of those mentioned above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Each individual compound of formula I named in the examples which follow is particularly suitable for the preparation of pharmaceutical formulations.

In the examples which follow "customary working up" signifies:

Sodium hydroxide solution is added, if necessary; the reaction mixture is extracted with an organic solvent, such as benzene, chloroform or methylene chloride; the organic phase is separated off, dried over sodium sulphate and filtered; the filtrate is evaporated; and the residue is purified by chromatography and/or crystallization.

The Rf values were obtained on silica gel using the solvent mixture indicated in the particular case: (A)=toluene/triethylamine, 8:2, (B)=methylene chloride/methanol, 9:1.

EXAMPLE 1

16.2 of p-trifluoromethylphenol is dissolved in 150 ml of 0.5 N ethanolic KOH and the solution is stirred for one hour at 20°. It is evaporated and the residue is taken up in 140 ml of DMF. A suspension of 23 g of 1-cyclopropyl-3-methylaminopropyl bromide in 40 ml of DMF is added; the mixture is heated at 130° for 1.5 hours and evaporated again; the residue is subjected to customary working up and 1-methylamino-3-cyclopropyl-3-p-trifluoromethylphenoxy-propane is obtained. Rf 0.22 (A).

EXAMPLE 2

16.2 g of p-trifluoromethylphenol is dissolved in 500 ml of absolute toluene; 7.1 ml of thallium-I ethylate is added; and the mixture is stirred for 1 hour at 20°. After evaporating, the residue is dissolved in 100 ml of absolute acetonitrile; 28.3 g of 1-cyclopropyl-3-methylaminopropyl p-toluene-sulphonate is added; and the mixture is boiled for 3 hours, with stirring, and evaporated. After the customary working up, 1-methylamino-3-cyclopropyl-3-p-trifluoromethylphenoxy-propane is obtained. Rf 0.22 (A).

EXAMPLE 3

2.7 g of diethyl azodicarboxylate is dissolved in 25 ml of THF; 4 g of triphenylphosphine is added with cooling and stirring; and a solution of 2.1 g of 1-cyclopropyl-3-methyl-amino-propan-1-ol in 10 ml of THF and then a solution of 1.4 g of p-trifluoromethyl-phenol in 10 ml of THF are then added dropwise and the resulting mixture is stirred for 2 hours at 0°. After standing overnight at 20°, the mixture is subjected to the customary working up. 1-Methylamino-3-cyclopropyl-3-p-trifluoromethylphenoxy-propane is obtained. Rf 0.22 (A).

EXAMPLE 4

200 ml of 50% aqueous sodium hydroxide solution and 1 g of triethylbenzylammonium chloride are added to a solution of 16.2 g of p-trifluoromethylphenol in 100 ml of $CH_2Cl_2$; 17.7 g of 1-cyclopropyl-3-methylaminopropyl chloride is added dropwise with stirring; and the resulting mixture is stirred for a further one hour.

After the customary working up, 1-methylamino-3-cyclopropyl-3-p-trifluoromethylphenoxy-propane is obtained. Rf 0.22 (A).

EXAMPLE 5 to 111

The following compounds are obtained analogously to Example 1, 2, 3 or 4 from the corresponding phenols of formula II and the corresponding amines of formula III (for example 1-cyclopropyl-3-methylamino-propan-1-ol or 1-cyclopropyl-3-methylaminopropyl chloride, bromide or iodide, 1-cyclopropyl-3-dimethyl-amino-propan-1-ol or 1-cyclopropyl-3-dimethylamino-propyl chloride, bromide or iodide, or 1-cyclopropyl-3-N-benzyl-N-methylamino-propan-1-ol or 1-cyclopropyl-3-N-benzyl-N-methylamino-propyl chloride, bromide or iodide):

5. 1-Methylamino-3-cyclopropyl-3-phenoxy-propane, Rf 0.4 (methylene chloride/triethylamine, 8:2).
6. 1-Methylamino-3-cyclopropyl-3-o-fluorophenoxy-propane.
7. 1-Methylamino-3-cyclopropyl-3-m-fluorophenoxy-propane.
8. 1-Methylamino-3-cyclopropyl-3-p-fluorophenoxy-propane, hydrochloride, melting point 178°–181°.
9. 1-Methylamino-3-cyclopropyl-3-o-chlorophenoxy-propane.
10. 1-Methylamino-3-cyclopropyl-3-m-chlorophenoxy-propane.
11. 1-Methylamino-3-cyclopropyl-3-p-chlorophenoxy-propane, Rf 0.4 (methylene chloride/triethylamine, 8:2).
12. 1-Methylamino-3-cyclopropyl-3-p-bromophenoxy-propane.
13. 1-Methylamino-3-cyclopropyl-3o-tolyloxy-propane.
14. 1-Methylamino-3-cyclopropyl-3-m-tolyloxy-propane.
15. 1-Methylamino-3-cyclopropyl-3-p-tolyloxy-propane, Rf 0.3 (methylene chloride/triethylamine,8:2).
16. 1-Methylamino-3-cyclopropyl-3-p-n-butylphenoxy-propane.
17. 1-Methylamino-3-cyclopropyl-3-o-methoxy-phenoxy-propane, Rf 0.3 (methylene chloride/triethylamine, 8:2).
18. 1-Methylamino-3-cyclopropyl-3-m-methoxy-phenoxy-propane, Rf 0.4 (chloroform/triethylamine, 8:2).

19. 1-Methylamino-3-cyclopropyl-3-p-methoxyphenoxy-propane, Rf 0.43 (chloroform/triethylamine, 8:2).
20. 1-Methylamino-3-cyclopropyl-3-p-n-butoxyphenoxy-propane.
21. 1-Methylamino-3-cyclopropyl-3-o-allylphenoxy-propane, Rf 0.58 (chloroform/triethylamine, 8:2).
22. 1-Methylamino-3-cyclopropyl-3-m-allyloxyphenoxy-propane.
23. 1-Methylamino-3-cyclopropyl-3-p-allyloxyphenoxy-propane.
24. 1-Methylamino-3-cyclopropyl-3-p-(2-methylallyloxy)phenoxy-propane.
25. 1-Methylamino-3-cyclopropyl-3-o-methylthiophenoxy-propane.
26. 1-Methylamino-3-cyclopropyl-3-m-methylthiophenoxy-propane.
27. 1-Methylamino-3-cyclopropyl-3-p-methylthiophenoxy-propane, Rf 0.60 (chloroform/triethylamine, 8:2).
28. 1-Methylamino-3-cyclopropyl-3-p-n-butylthiophenoxy-propane.
29. 1-Methylamino-3-cyclopropyl-3-o-hydroxyphenoxy-propane.
30. 1-Methylamino-3-cyclopropyl-3-m-hydroxyphenoxy-propane.
31. 1-Methylamino-3-cyclopropyl-3-p-hydroxyphenoxy-propane.
32. 1-Methylamino-3-cyclopropyl-3-o-mercaptophenoxy-propane.
33. 1-Methylamino-3-cyclopropyl-3-m-mercaptopbenoxy-propane.
34. 1-Methylamino-3-cyclopropyl-3-p-mercaptophenoxy-propane.
35. 1-Methylamino-3-cyclopropyl-3-o-cyanophenoxy-propane.
36. 1-Methylamino-3-cyclopropyl-3-m-cyanophenoxy-propane.
37. 1-Methylamino-3-cyclopropyl-3-p-cyanophenoxy-propane, Rf 0.3 (chloroform/triethylamine, 8:2).
38. 1-Methylamino-3-cyclopropyl-3-(3,4-dimethoxyphenoxy)-propane, Rf 0.35 (chloroform).
39. 1-Methylamino-3-cyclopropyl-3-(3,4-methylenedioxyphenoxy)-propane, Rf 0.45 (chloroform/triethylamine, 8:2).
40. 1-Methylamino-3-cyclopropyl-3-o-trifluoromethylphenoxy-propane.
41. 1-Methylamino-3-cyclopropyl-3-m-trifluoromethylphenoxy-propane.
42. 1-Dimethylamino-3-cyclopropyl-3-phenoxy-propane, Rf 0.75 (chloroform/triethylamine, 8:2).
43. 1-Dimethylamino-3-cyclopropyl-3-o-fluorophenoxy-propane.
44. 1-Dimethylamino-3-cyclopropyl-3-m-fluorophenoxy-propane, Rf 0.75 (chloroform/triethylamine, 8:2).
45. 1-Dimethylamino-3-cyclopropyl-3-p-fluorophenoxy-propane.
46. 1-Dimethylamino-3-cyclopropyl-3-o-chlorophenoxy-propane.
47. 1-Dimethylamino-3-cyclopropyl-3-m-chlorophenoxy- propane.
48. 1-Dimethylamino-3-cylopropyl-3-p-chlorophenoxypropane, Rf 0.5 (acetone/triethylamine, 9:1).
49. 1-Dimethylamino-3-cyclopropyl-3-p-bromophenoxy-propane.
50. 1-Dimethylamino-3-cyclopropyl-3-o-tolyloxy-propane.
51. 1-Dimethylamino-3-cyclopropyl-3-m-tolyloxy-propane.
52. 1-Dimethylamino-3-cyclopropyl-3-p-tolyloxy-propane, Rf 0.46 (toluene/triethylamine, 9:1).
53. 1-Dimethylamino-3-cyclopropyl-3-o-methoxyphenoxy-propane, Rf 0.25 (A).
54. 1-Dimethylamino-3-cyclopropyl-3-m-methoxyphenoxy-propane, Rf 0.7 (chloroform/triethylamine, 8:2).
55. 1-Dimethylamino-3-cyclopropyl-3-p-methoxyphenoxy-propane, Rf 0.41 (toluene/triethylamine, 9:1).
56. 1-Dimethylamino-3-cyclopropyl-3-o-allyloxyphenoxy-propane, Rf 0.48 (toluene/triethylamine, 9:1).
57. 1-Dimethylamino-3-cyclopropyl-3-m-allyloxyphenoxy-propane.
58. 1-Dimethylamino-3-cyclopropyl-3-p-allyloxyphenoxy-propane.
59. 1-Dimethylamino-3-cyclopropyl-3-o-methylthiophenoxy-propane.
60. 1-Dimethylamino-3-cyclopropyl-3-m-methylthiophenoxy-propane.
61. 1-Dimethylamino-3-cyclopropyl-3-p-methylthiophenoxy-propane, Rf 0.45 (toluene/triethylamine, 9:1).
62. 1-Dimethylamino-3-cyclopropyl-3-o-hydroxyphenoxy-propane.
63. 1-Dimethylamino-3-cyclopropyl-3-m-hydroxyphenoxy-propane.
64. 1-Dimethylamino-3-cyclopropyl-3-p-hydroxyphenoxy-propane.
65. 1-Dimethylamino-3-cyclopropyl-3-o-mercaptophenoxy-propane.
66. 1-Dimethylamino-3-cyclopropyl-3-m-mercaptophenoxy-propane.
67. 1-Dimethylamino-3-cyclopropyl-3-p-mercaptophenoxy-propane.
68. 1-Dimethylamino-3-cyclopropyl-3-o-cyanophenoxy-propane.
69. 1-Dimethylamino-3-cyclopropyl-3-m-cyanophenoxy-propane.
70. 1-Dimethylamino-3-cyclopropyl-3-p-cyanophenoxy-propane.
71. 1-Dimethylamino-3-cyclopropyl-3-(3,4-dimethoxyphenoxy)-propane.
72. 1-Dimethylamino-3-cyclopropyl-3-(3,4-methylenedioxy-phenoxy)-propane, Rf 0.42 (toluene/triethylamine, 9:1).
73. 1-Dimethylamino-3-cyclopropyl-3-o-trifluoromethylphenoxy-propane.
74. 1-Dimethylamino-3-cyclopropyl-3-m-trifluoromethylphenoxy-propane.
75. 1-Dimethylamino-3-cyclopropyl-3-p-trifluoromethylphenoxy-propane, Rf 0.44 (toluene/triethylamine, 9:1).
76. 1-N-Benzyl-N-methylamino-3-cyclopropyl-3-phenoxy-propane.
77. 1-N-Benzyl-N-methylamino-3-cyclopropyl-3-o-fluorophenoxy-propane.
78. 1-N-Benzyl-N-methylamino-3-cyclopropyl-3-m-fluorophenoxy-propane.
79. 1-N-Benzyl-N-methylamino-3-cyclopropyl-3-p-fluorophenoxy-propane, Rf 0.53 (B).
80. 1-N-Benzyl-N-methylamino-3-cyclopropyl-3-o-chlorophenoxy-propane.
81. 1-N-Benzyl-N-methylamino-3-cyclopropyl-3-m-chlorophenoxy-propane.

82. 1-N-Benzyl-N-methylamino-3-cyclopropyl-3-p-chlorophenoxy-propane.
83. 1-N-Benzyl-N-methylamino-3-cyclopropyl-3-p-bromophenoxy-propane.
84. 1-N-Benzyl-N-methylamino-3-cyclopropyl-3-o-tolyloxy-propane.
85. 1-N-Benzyl-N-methylamino-3-cyclopropyl-3-m-tolyloxy-propane.
86. 1-N-Benzyl-N-methylamino-3-cyclopropyl-3-p-tolyloxy-propane.
87. 1-N-Benzyl-N-methylamino-3-cyclopropyl-3-o-methoxyphenoxy-propane.
88. 1-N-Benzyl-N-methylamino-3-cyclopropyl-3-m-methoxyphenoxy-propane.
89. 1-N-Benzyl-N-methylamino-3-cyclopropyl-3-p-methoxyphenoxy-propane, Rf 0.81 (B).
90. 1-N-Benzyl-N-methylamino-3-cyclopropyl-3-o-allyloxyphenoxy-propane.
91. 1-N-Benzyl-N-methylamino-3-cyclopropyl-3-m-allyloxyphenoxy-propane.
92. 1-N-Benzyl-N-methylamino-3-cyclopropyl-3-p-allyloxyphenoxy-propane.
93. 1-N-Benzyl-N-methylamino-3-cyclopropyl-3-o-methylthiophenoxy-propane.
94. 1-N-Benzyl-N-methylamino-3-cyclopropyl-3-m-methylthiophenoxy-propane.
95. 1-N-Benzyl-N-methylamino-3-cyclopropyl-3-p-methylthiophenoxy-propane, Rf 0.65 (B).
96. 1-N-Benzyl-N-methylamino-3-cyclopropyl-3-o-hydroxyphenoxy-propane.
97. 1-N-Benzyl-N-methylamino-3-cyclopropyl-3-m-hydroxyphenoxy-propane.
98. 1-N-Benzyl-N-methylamino-3-cyclopropyl-3-p-hydroxyphenoxy-propane.
99. 1-N-Benzyl-N-methylamino-3-cyclopropyl-3-o-mercaptophenoxy-propane.
100. 1-N-Benzyl-N-methylamino-3-cyclopropyl-3-m-mercaptophenoxy-propane.
101. 1-N-Benzyl-N-methylamino-3-cyclopropyl-3-p-mercaptophenoxy-propane.
102. 1-N-Benzyl-N-methylamino-3-cyclopropyl-3-o-cyanophenoxy-propane.
103. 1-N-Benzyl-N-methylamino-3-cyclopropyl-3-m-cyanophenoxy-propane.
104. 1-N-Benzyl-N-methylamino-3-cyclopropyl-3-p-cyanophenoxy-propane.
105. 1-N-Benzyl-N-methylamino-3-cyclopropyl-3-(3,4-dimethoxyphenoxy)-propane.
106. 1-N-Benzyl-N-methylamino-3-cyclopropyl-3-(3,4-methylenedioxyphenoxy)-propane.
107. 1-N-Benzyl-N-methylamino-3-cyclopropyl-3-o-trifluoromethylphenoxy-propane.
108. 1-N-Benzyl-N-methylamino-3-cyclopropyl-3-m-trifluoromethylphenoxy-propane.
109. 1-N-Benzyl-N-methylamino-3-cyclopropyl-3-p-trifluoromethylphenoxy-propane.
110. 1-N-Ethyl-N-methylamino-3-cyclopropyl-3-p-trifluoromethylphenoxy-propane.
111. 1-N-n-Butyl-N-methylamino-3-cyclopropyl-3-p-trifluoromethylphenoxy-propane.

EXAMPLE 112

A solution of 4.14 g of 1-p-toluenesulphonyloxy-3-cyclopropyl-3-p-trifluoromethylphenoxy-propane (obtainable by reaction of cyclopropyl cyanide with 2,2-diethoxyethylmagnesium bromide and subsequent hydrolysis of the reaction product to 3,3-diethoxy-1-cyclopropylpropan-1-one; reduction of the latter to 3,3-diethoxy-1-cyclopropyl-propan-1-ol; reaction of the latter with p-trifluoromethylphenol analogously to Example 3; hydrolysis of the reaction product to 3-cyclopropyl-3-p-trifluoromethylphenoxy-propanal; reduction of the latter to 3-cyclopropyl-3-p-trifluoromethylphenoxy-propan-1-ol; and tosylation of the latter) and 30 g of methylamine in 100 ml of methanol is heated at 120° in an autoclave for 2 hours. After cooling and customary working up, 1-methylamino-3-cyclopropyl-3-p-trifluoromethylphenoxy-propane is obtained. Rf 0.22 (A).

EXAMPLES 113 TO 219

The compounds indicated in Examples 5 to 111 are obtained analogously to Example 112 by reacting the corresponding 1-p-toluenesulphonyloxy-, 1-chloro- or 1-bromo-3-cyclopropyl-3-aryloxy-propanes with methylamine, dimethylamine, N-benzyl-N-methylamine, N-ethyl-N-methylamine or N-n-butyl-N-methylamine. With the less volatile amines, it is possible to dispense with the application of pressure and/or to use higher-boiling solvents, such as isopropanol or n-butanol.

EXAMPLE 220

2.3 g of sodium is dissolved in 250 ml of ethanol, and 24.2 g of 3-cyclopropyl-3-p-trifluoromethylphenoxy-propene (obtainable from 3-cyclopropyl-3-hydroxypropene and p-trifluoromethylphenol) and then a solution of 100 g of methylamine in 300 ml of ethanol are added and the mixture is heated at 100° in an autoclave for 72 hours. After evaporating and subjecting the residue to the customary working up, 1-methylamino-3-cyclopropyl-3-p-trifluoromethylphenoxypropane is obtained. Rf 0.22 (A).

EXAMPLES 221 TO 327

The compounds indicated in Examples 5 to 111 are obtained analogously to Example 220 by an addition reaction of the abovementioned amines with the corresponding 3-cyclopropyl-3-aryloxy-propenes.

EXAMPLE 328

A solution of 2.59 g of 1-amino-3-cyclopropyl-3-p-trifluoromethylphenoxy-propane (obtainable by a condensation reaction of ethyl cyclopropanecarboxylate with ethyl acetate to give ethyl 3-cyclopropyl-propan-3-on-1-oate; reduction of the latter to ethyl 3-cyclopropyl-propan-3-ol-1-oate; reaction of the latter with p-trifluoromethylphenol analogously to Example 3, to give ethyl 3-cyclopropyl-3-p-trifluoromethylphenoxy-propanoate; reaction with $NH_3$ to give the amide; and reduction of the latter with $LiAlH_4$) and 1.5 g of benzaldehyde in 25 ml of toluene is boiled for one hour under a water separator. The solution of the resulting 1-benzylideneamino-3-cyclopropyl-3-p-trifluoromethyl-phenoxy-propane is heated with 5 g of methyl iodide for 12 hours at 150° in a tube and then evaporated. The resulting quaternary salt is boiled for 10 minutes in 90% ethanol. The mixture is again evaporated, the residue is taken up in dilute hydrochloric acid and the benzaldehyde which has been split off is removed by extraction with ether. The acid, aqueous solution is rendered alkaline with sodium hydroxide solution and worked up in the customary manner. 1-Methylamino-3-cyclopropyl-3-p-trifluoromethylphenoxypropane is obtained. Rf 0.22 (A).

EXAMPLES 329 TO 365

The compounds indicated in Examples 5 to 41 are obtained analogously to Example 328 by methylation of the corresponding 1-amino-3-cyclopropyl-3-aryloxy-propanes.

EXAMPLE 366

A mixture of 29.6 g of 1-amino-3-cyclopropyl-3-p-trifluoromethylphenoxy-propane hydrochloride, 50 ml of formic acid, 7 g of sodium formate and 40 ml of 40% formaldehyde solution is heated at 60° for 3 hours and then at 100° for 12 hours. After the customary working up, 1-dimethylamino-3-cyclopropyl-3-p-trifluoromethylphenoxy-propane is obtained.

EXAMPLES 367 TO 400

The compounds described in Examples 42 to 75 are obtained analogously to Example 366 from the corresponding 1-amino-3-cyclopropyl-3-aryloxy-propanes with formic acid/sodium formate/formaldehyde.

EXAMPLE 401

A mixture of 29.8 g of 1-N-methyl-N-cyanoamino-3-cyclopropyl-3-p-trifluoromethylphenoxy-propane (obtainable by reacting 1-dimethylamino-3-cyclopropyl-3-p-trifluoromethylphenoxy-propane with BrCN), 300 g of KOH, 250 ml of water and 1,200 ml of ethylene glycol is boiled for 20 hours, cooled and subjected to the customary working up. 1-Methylamino-3-cyclopropyl-3-p-trifluoromethylphenoxy-propane is obtained. Rf 0.22 (A).

EXAMPLES 402 TO 438

The compounds indicated in Examples 5 to 41 are obtained analogously to Example 401 by reacting the corresponding 1-N-methyl-N-cyano-amino-3-cyclopropyl-3-aryloxy-propanes with KOH.

EXAMPLE 439

A solution of 3.69 g of 1-N-methyl-N-trifluoroacetylamino-3-cyclopropyl-3-p-trifluoromethyl-phenoxy-propane (obtainable by reacting 1-p-toluenesulphonyloxy-3-cyclopropyl-3-p-trifluoromethyl-phenoxy-propane with N-methyl-trifluoroacetamide) in 50 ml of 1N ethanolic KOH solution is boiled for one hour. The solution is evaporated and subjected to the customary working up, and 1-methylamino-3-cyclopropyl-3-p-trifluoromethylphenoxy-propane is obtained. Rf 0.22 (A).

EXAMPLES 440 TO 476

The compounds indicated in Examples 5 to 41 are obtained analogously to Example 439 from the corresponding 1-N-methyl-N-acylamino-3-cyclopropyl-3-aryloxy-propanes by alkaline hydrolysis.

EXAMPLE 477

A solution of 28.7 g of 3-cyclopropyl-3-p-trifluoromethylphenoxy-propanoic acid N-methylamide (obtainable by reacting the corresponding ethyl ester with methylamine) in 500 ml of THF is added dropwise, with stirring, to a suspension of 7.6 g of LiAlH$_4$ in 250 ml of absolute THF. The mixture is boiled for 16 hours and, with cooling, ethyl acetate and then 32% sodium hydroxide solution are added. The mixture is subjected to the customary working up and 1-methylamino-3-cyclopropyl-3-p-trifluoromethyl-phenoxy-propane is obtained. Rf 0.22 (A).

EXAMPLES 478 TO 584

The compounds indicated in Examples 5 to 111 are obtained analogously to Example 477, by reduction of the corresponding 3-cyclopropyl-3-aryloxy-propanoic acid N-methylamides, N,N-dimethylamides, N-benzyl-N-methylamides, N-ethyl-N-methylamides or N-n-butyl-N-methylamides.

EXAMPLE 585

A solution of 27.1 g of 1-methylimino-3-cyclopropyl-3-trifluoro-methylphenoxy-propane (obtainable from 3-cyclopropyl-3-p-trifluoromethylphenoxy-propanal and methylamine) in 250 ml of dioxane is hydrogenated on 2 g of 2% Pd-C at 20° and under normal pressure until 1 mole of hydrogen has been taken up. The mixture is filtered, the filtrate is evaporated and 1-methylamino-3-cyclopropyl-3-p-trifluoromethylphenoxy-propane is obtained. Rf 0.22 (A).

EXAMPLES 586 TO 622

The compounds indicated in Examples 5 to 41 are obtained analogously to Example 585 by hydrogenation of the corresponding 1-methylimino-3-cyclopropyl-3-aryloxy-propanes.

EXAMPLE 623

With stirring and cooling, 30 g of formic acid is added dropwise to 27.3 g of 1-methylamino-3-cyclopropyl-3-p-trifluoromethylphenoxy-propane, and 7 g of 25% formaldehyde solution is then added dropwise at 20°. The mixture is heated on a waterbath until the evolution of gas has ceased and is cooled, poured onto ice and subjected to the customary working up, and 1-dimethylamino-3-cyclopropyl-3-p-trifluoromethylphenoxy-propane is obtained.

EXAMPLE 624

17.1 g of benzyl bromide and 26 g of anhydrous potassium carbonate are added to a solution of 27.3 g of 1-methylamino-3-cyclopropyl-3-p-trifluoromethylphenoxy-propane in 1 l of absolute toluene, the mixture is boiled for 20 hours, cooled, poured into water and subjected to the customary working up and 1-N-benzyl-N-methylamino-3-cyclopropyl-3-p-trifluoromethylphenoxy-propane is obtained.

EXAMPLE 625

0.4 g of K$_2$CO$_3$ is added to a solution of 3.63 g of 1-N-benzyl-N-methylamino-3-cyclopropyl-3-p-trifluoromethylphenoxy-propane in 70 ml of toluene. 5.9 g of 2,2,2-trichloroethyl chloroformate is added dropwise, with stirring and boiling. The resulting mixture is boiled for a further 3 hours and poured onto ice and the organic phase is separated off, dried over MgSO$_4$ and evaporated. The resulting crude 1-N-methyl-N-(2,2,2-trichloroethoxy-carbonyl)-amino-3-cyclopropyl-3-p-trifluoromethylphenoxy-propane (4.7 g) is introduced into 50 ml of 95% acetic acid. 8.5 g of zinc powder is added, the mixture is stirred for 3 hours at 25° and filtered, the filtrate is subjected to the customary working up and 1-methylamino-3-cyclopropyl-3-p-trifluoromethyl-phenoxy-propane is obtained. Rf 0.22 (A).

EXAMPLE 626

A solution of 36.3 g of 1-N-benzyl-N-methylamino-3-cyclopropyl-3-p-trifluoromethyl-phenoxy-propane in 400 ml of methanol is hydrogenated on 3 g of 5% Pd-C at 20° and under 1 atmosphere until 0.1 mole of hydrogen has been taken up. The mixture is filtered, the filtrate is evaporated and 1-methylamino-3-cyclopropyl-3-p-trifluoromethyl-phenoxy-propane is obtained. Rf 0.22 (A).

EXAMPLE 627

A mixture of 1 g of 1-dimethylamino-3-cyclopropyl-3-p-methoxyphenoxy-propane and 1 g of pyridine hydrochloride is stirred for 3 hours at 160°. After the customary working up, 1-dimethylamino-3-cyclopropyl-3-p-hydroxyphenoxy-propane is obtained.

EXAMPLE 628

1-Dimethylamino-3-cyclopropyl-3-p-mercaptophenoxypropane is obtained analogously to Example 627, from 1-dimethylamino-3-cyclopropyl-3-p-methylthiophenoxy-propane and pyridine hydrochloride.

EXAMPLE 629

A mixture of 23.5 g of 1-dimethylamino-3-cyclopropyl-3-p-hydroxyphenoxy-propane, 100 ml of absolute ethanol and 200 ml of 0.5N ethanolic KOH is stirred for one hour at 20° and evaporated. The residue is dissolved in 250 ml of absolute DMF. 12.6 g of dimethyl sulphate is added in portions, with stirring. The mixture is boiled for two hours and evaporated; the residue is subjected to the customary working up; and 1-dimethylamino-3-cyclopropyl-3-p-methoxyphenoxy-propane is obtained.

EXAMPLE 630

1-Dimethylamino-3-cyclopropyl-3-p-methylthiophenoxy-propane is obtained analogously to Example 629 from 1-dimethylamino-3-cyclopropyl-3-p-mercaptophenoxy-propane and dimethyl sulphate.

The examples which follow relate to pharmaceutical formulations which contain amines of the formula I or their acid addition salts.

EXAMPLE A: TABLETS

A mixture of 1 kg of 1-methylamino-3-cyclopropyl-3-p-trifluoromethyl-phenoxy-propane hydrochloride, 4 kg of lactose, 1.2 kg of potato starch, 0.2 kg of talc and 0.1 kg of magnesium stearate is pressed into tablets in the conventional manner, in such a way that each tablet contains 10 mg of active ingredient.

EXAMPLE B: DRAGEES

Tablets are pressed analogously to Example A and these are then coated in the conventional manner with a coating consisting of sucrose, potato starch, talc, tragacanth and dyestuff.

EXAMPLE C: CAPSULES 2 kg of 1-methylamino-3-cyclopropyl-3-p-trifluoromethylphenoxy-propane hydrochloride is filled into hard gelatin capsules in the conventional manner, so that each capsule contains 20 mg of the active compound.

EXAMPLE D: AMPOULES

A solution of 1 kg of 1-methylamino-3-cyclopropyl-3-p-trifluoromethyl-phenoxy-propane hydrochloride in 30 l of twice distilled water is sterile-filtered, filled into ampoules and lyophilized under sterile conditions and the ampoules are sealed. Each ampoule contains 10 mg of active compound.

Tablets, dragees, capsules and ampoules which contain one or more of the other active compounds of formula I and/or their physiologically acceptable acid addition salts are obtainable analogously.

Particularly advantageous compounds are 1-dimethylamino-3-cyclopropyl-3-p-trifluoromethylphenoxy-propane as well as its physiologically acceptable acid addition salts such as its hydrochloride (m.p. 131°–132°) and its citrate (m.p. 102°–103°).

The preceding examples can be repeated with similar success by substituting the generically or specifically described reactants and/or operating conditions of this invenition for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cyclopropane derivative of the formula

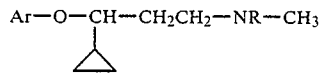

wherein Ar is phenyl or phenyl monosubstituted or polysubstituted by F, Cl, Br, $C_{1-4}$ alkyl, $C_{1-4}$ alkoxy, $C_{2-4}$ alkenyloxy, $C_{1-4}$ alkylthio, OH, SH, CN, methylenedioxy or $CF_3$; and R is H, $C_{1-4}$ alkyl or benzyl, or a physiologically acceptable acid addition salt thereof.

2. A compound of claim 1 wherein Ar is phenyl or phenyl substituted by F, Cl, $CH_3O$, $CH_2=CHCH_2O$, $CH_3S$, OH, SH, CN or $CF_3$ and R is H, $CH_3$ or benzyl.

3. A compound of claim 1, wherein Ar is m- or p-fluorophenyl, p-chlorophenyl, o-, m- or p-methoxyphenyl, o-allyloxyphenyl, p-methylthiophenyl or p-trifluoromethylphenyl and R is H, $CH_3$ or benzyl.

4. A compound of claim 1 wherein Ar is m- or p-fluorophenyl, p-chlorophenyl, o-, m- or p-methoxyphenyl, o-allyloxyphenyl, p-methylthiophenyl or p-trifluoromethylphenyl and R is H or $CH_3$.

5. A compound of claim 1 wherein Ar is o-methoxyphenyl or p-trifluoromethyl-phenyl and R is H, $CH_3$ or benzyl.

6. A compound of claim 1 wherein Ar is p-trifluoromethylphenyl and R is H, $CH_3$ or benzyl.

7. 1-Methylamino-3-cyclopropyl-3-p-trifluoromethyl-phenoxypropane, a compound of claim 1.

8. 1 Dimethylamino-3-cyclopropyl-3-p-trifluoromethylphenoxy-propane, a compound of claim 1, and its hydrochloride.

9. A pharmaceutical composition for treating depression, comprising an antidepressantly effective amount of a compound of claim 1 and a pharmaceutically acceptable adjuvant.

10. A pharmaceutical composition of claim 9 wherein the amount of active compound is 2–500 mg.

11. A method of treating depression in a patient in need of such treatment comprising administering an antidepressantly effective amount of a compound of claim 1 to the patient.

* * * * *